(12) United States Patent
Blackwood et al.

(10) Patent No.: US 9,696,372 B2
(45) Date of Patent: Jul. 4, 2017

(54) MULTIDIMENSIONAL STRUCTURAL ACCESS

(71) Applicant: FEI Company, Hillsboro, OR (US)

(72) Inventors: Jeffrey Blackwood, Portland, OR (US); Sang Hoon Lee, Hillsboro, OR (US); Michael Schmidt, Gresham, OR (US); Stacey Stone, Beaverton, OR (US); Karey Holland, North Plains, OR (US)

(73) Assignee: FEI Company, Hillsboro, OR (US)

( * ) Notice: Subject to any disclaimer, the term of this patent is extended or adjusted under 35 U.S.C. 154(b) by 89 days.

(21) Appl. No.: 14/432,712

(22) PCT Filed: Oct. 4, 2013

(86) PCT No.: PCT/US2013/063556
§ 371 (c)(1),
(2) Date: Mar. 31, 2015

(87) PCT Pub. No.: WO2014/055935
PCT Pub. Date: Apr. 10, 2014

(65) Prior Publication Data
US 2015/0260784 A1   Sep. 17, 2015

Related U.S. Application Data

(60) Provisional application No. 61/710,668, filed on Oct. 5, 2012.

(51) Int. Cl.
*G01R 31/305* (2006.01)
*G01R 31/265* (2006.01)
(Continued)

(52) U.S. Cl.
CPC ......... *G01R 31/2653* (2013.01); *G01N 1/286* (2013.01); *G01N 1/32* (2013.01);
(Continued)

(58) Field of Classification Search
CPC ........ G01N 1/286; G01N 1/32; G01R 31/307; G01R 31/2653; G01R 31/04;
(Continued)

(56) References Cited

U.S. PATENT DOCUMENTS 5,435,850 A   7/1995 Rasmussen
5,851,413 A   12/1998 Casella et al.
(Continued)

FOREIGN PATENT DOCUMENTS

JP   2003114252 A   4/2003

*Primary Examiner* — Patrick Assouad
*Assistant Examiner* — Demetrius Pretlow
(74) *Attorney, Agent, or Firm* — Scheinberg & Associates, P.C.; John B. Kelly; Michael O. Scheinberg

(57) ABSTRACT

Multiple planes within the sample are exposed from a single perspective for contact by an electrical probe. The sample can be milled at a non-orthogonal angle to expose different layers as sloped surfaces. The sloped edges of multiple, parallel conductor planes provide access to the multiple levels from above. The planes can be accessed, for example, for contacting with an electrical probe for applying or sensing a voltage. The level of an exposed layer to be contacted can be identified, for example, by counting down the exposed layers from the sample surface, since the non-orthogonal mill makes all layers visible from above. Alternatively, the sample can be milled orthogonally to the surface, and then tilted and/or rotated to provide access to multiple levels of the device. The milling is preferably performed away from the region of interest, to provide electrical access to the region while minimizing damage to the region.

21 Claims, 7 Drawing Sheets

(51) Int. Cl.
*G01N 1/28* (2006.01)
*H01L 21/66* (2006.01)
*G01N 1/32* (2006.01)
*H01J 37/30* (2006.01)
*H01J 37/153* (2006.01)
*G01R 31/307* (2006.01)
*G01R 31/28* (2006.01)
*G01R 31/312* (2006.01)

(52) U.S. Cl.
CPC .......... *G01R 31/307* (2013.01); *H01J 37/153* (2013.01); *H01J 37/3005* (2013.01); *H01L 22/14* (2013.01); *G01R 31/2808* (2013.01); *G01R 31/2898* (2013.01); *G01R 31/312* (2013.01); *H01J 2237/208* (2013.01); *H01J 2237/24564* (2013.01); *H01J 2237/2817* (2013.01); *H01J 2237/31749* (2013.01); *H01L 2924/0002* (2013.01)

(58) Field of Classification Search
CPC  G01R 31/2884; G01R 31/305; G01R 31/311; G01R 1/071; G01R 31/2601; G01R 31/2851; G01R 31/308; G01R 1/04; G01R 31/2648; G01R 31/2808; G01R 31/302; G01R 31/303; G01R 31/312; H01J 37/3005; H01J 37/153; H01L 22/14
USPC .................. 324/754.22, 754.21–754.23, 324/762.01–762.1; 250/309–311
See application file for complete search history.

(56) References Cited

U.S. PATENT DOCUMENTS

| | | | |
|---|---|---|---|
| 6,288,558 B1* | 9/2001 | Zimmermann | G01R 31/275 324/754.11 |
| 6,373,070 B1 | 4/2002 | Rasmussen | |
| 6,727,500 B1* | 4/2004 | Berger | H01J 37/3056 250/492.2 |
| 6,734,687 B1* | 5/2004 | Ishitani | G01R 31/311 324/750.19 |
| 2003/0086097 A1 | 5/2003 | Finarov | |
| 2003/0183776 A1* | 10/2003 | Tomimatsu | G01N 1/28 250/442.11 |
| 2005/0064610 A1* | 3/2005 | Bruley | G01R 31/307 438/14 |
| 2006/0091325 A1* | 5/2006 | Moore | B82Y 15/00 250/492.21 |
| 2006/0186874 A1* | 8/2006 | Mackin | G01N 3/42 324/754.1 |
| 2006/0292705 A1 | 12/2006 | Hegde et al. | |
| 2008/0073535 A1 | 3/2008 | Hong et al. | |
| 2008/0142711 A1* | 6/2008 | Lundquist | G01Q 30/02 250/307 |
| 2008/0185517 A1* | 8/2008 | Frosien | H01J 37/3056 250/289 |
| 2008/0245965 A1 | 10/2008 | Sugiyama et al. | |
| 2010/0092070 A1* | 4/2010 | Young | G06T 7/0042 382/151 |
| 2010/0163727 A1* | 7/2010 | Bell | G01R 31/307 250/307 |
| 2013/0240353 A1 | 9/2013 | Watanabe et al. | |
| 2014/0091311 A1 | 4/2014 | Jeon et al. | |
| 2015/0048815 A1 | 2/2015 | Barends et al. | |
| 2015/0243478 A1 | 8/2015 | Lee et al. | |

* cited by examiner

MULTIDIMENSIONAL STRUCTURAL ACCESS

TECHNICAL FIELD OF THE INVENTION

The present invention relates to processing of multidimensional, microscopic structures to provide electrical access to internal structures.

BACKGROUND OF THE INVENTION

As semiconductor fabrication processes pack more circuitry into smaller packages, integrated circuit (IC) designs are becoming more three-dimensional (3D). It is difficult to measure, analyze and locate faults in 3D microscopic (including nanoscopic) structures.

An engineer will typically identify a region-of-interest (ROI) that he wants to investigate, based upon, for example, aberrant electrical behavior of a circuit component. Most ROIs in conventional ICs are confined to a small volume of the device in a planar region. For example, a static random access memory (SRAM) or a conventional "not-and" (NAND) flash cell each occupies a distinct X and Y location, with a small volume of active area in the Z direction. An engineer typically identifies the ROI by starting with a logic bit or gate address, which can then be mapped to a physical X/Y location in an active region of the structure.

The ROI is often buried below layers of insulator and conductors. Once the ROI is identified, the circuit can be "deprocessed," that is, overlying structures can be removed, to expose the ROI. Current deprocessing techniques typically provide access to the structure in a planar fashion—ion beam milling creates surfaces orthogonal to the device surface in order to allow imaging, probing, or other localization techniques. Likewise cleaving the wafer or parallel-lapping deprocessing provides access to a plane of the structure.

Techniques to analyze the ROI include, for example, micro-probing, in which conductive probes are contacted to the conductors on the IC to apply and/or measure voltages or currents. Another technique for analyzing a ROI is voltage contrast imaging, in which a charged particle beam image, which is sensitive to any voltage on the imaged surface, is obtained while a voltage is applied to a part of the circuit. Other analysis techniques include scanning probe microscopy, such as scanning-capacitance microscopy, in which a fine probe is scanned above the region of interest and the electrical or physical behavior of the probe is monitored. As used herein, analysis techniques include imaging techniques.

Current techniques map locations on an integrated circuit as if the device were a city in which buildings have only one floor—simply getting the street address is sufficient to deliver the mail to the correct location. Emerging three dimensional (3D) IC fabrication technologies do not constrain the active area (i.e., transistor or memory cell) to one plane in the Z direction—active areas occupy many levels of 3D devices. The city map is now populated by skyscrapers—the address information needs to reference to which floor the mail is to be delivered. Rather than identify a 2D region of interest, an engineer will require distinct isolation of a volume-of-interest (VOI) in three dimensions.

For 3D IC structures, prior art techniques that provide planar access are inherently limited to two dimensions of the structure, resulting in either more complicated or impossible final access to the VOI.

SUMMARY OF THE INVENTION

An embodiment of the present invention provides electrical access to internal components of a three-dimensional structure.

Multiple planes within the sample are exposed from a single perspective for imaging and/or probing. For example, the sample can be milled at a non-orthogonal angle to expose different layers as sloped surfaces. The non-orthogonal milling exposes edges of multiple, parallel conductor planes to provide access to multiple levels from above. Once exposed, the planes can be accessed, for example, for contacting with an electrical probe for applying or sensing a voltage. The level of an exposed layer to be contacted can be identified, for example, by counting down the exposed layers from the sample surface, since the non-orthogonal mill makes all layers visible from above. Alternatively, the sample can be milled orthogonally to the surface, and then tilted and/or rotated to provide access to multiple levels of the device. The milling is preferably performed away from the region of interest, to provide electrical access to the region while minimizing damage to the region.

Additional processing can be applied to the exposed layers, for example, using circuit edit-type techniques, such as passivating, depositing an insulator on part of the sample, cutting circuits, and depositing conductors to change behavior or creating probing points.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

Figure 1:
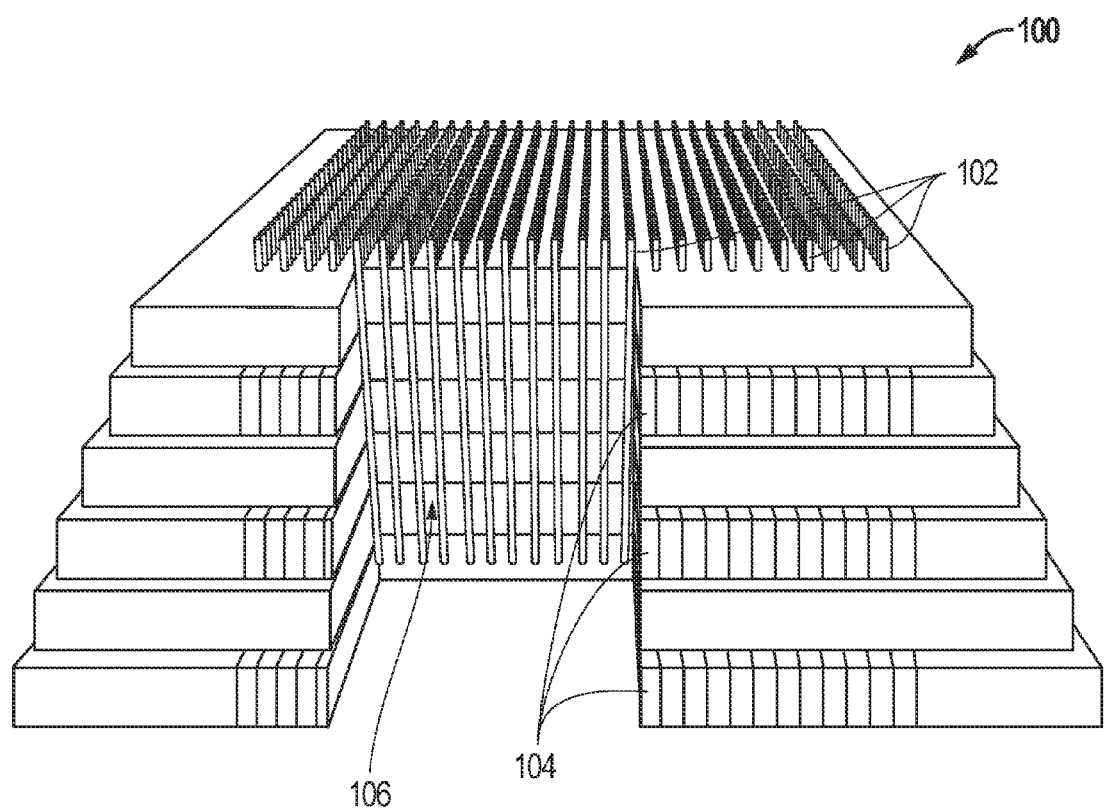
FIG. 1 is shows a 3D storage device having a trench milled therein to expose a vertical face.

In one conventional analysis of two-dimensional processing, a region of interest is exposed by ion beam milling and electrical probes are contacted to the region of interest, typically from above. The region of interest can be viewed from above using an electron beam with voltage applied for voltage contrast imaging. This works well for 2D structures, but for newer structures having transistors or memory cells on many layers, it is very difficult to access the correct layer in the stack when one is looking at the structure from the top. In accordance with an aspect of some embodiments of the invention, the sample is milled and/or tilted so that multiple planes within the sample are exposed from a single perspective, typically from above, for imaging or probing.

Also, most prior art cross-sectional techniques are preformed through the region of interest, such as the particular failing part in a failure analysis. Due to the increased complexity of new 3D structures it is advantageous to keep as much of the structure around the region of interest intact during analysis. In accordance with an aspect of some embodiments of the invention, the milling exposes the electrical connections to a ROI, and keeps much of the ROI intact while providing electrical access to the ROI. As used herein, the term ROI or region of interest is also used to refer to a volume of interest or VOI.

Off-angle mills, preferably from about 30° to about 45° from a normal to the surface, spatially separate out the layers in a top-down view so that they may be viewed and accessed. The greater the deviation from orthogonality, the more surface is exposed to a vertical view from above the sample. A normal to the exposed area has a component in the vertical direction, so that the horizontal layer can be observed from above and contacted from above by an electrical probe. A tilted sample can provide the same effect, separating out layers for viewing and exposing them in a top down view.

By milling in an orientation that is not orthogonal to the work piece surface or tilting the structure after a vertical mill, users can see the electrical addressing connections to the ROI using an optical microscope or a SEM and can provide therefore electrical signals to the ROI without being able to actually see it. The tapered mills or tilted sample provide access to the sample in angled sidewalls to allow electrical localization of a defect or other ROI. Access to the angled side wall allows probing the plane at the z-depth of interest, while still providing access to the vertical conductor. Embodiments of the invention provide access to X, Y, and Z localization from a top-view of a sample, and allow electrical probing access to the VOI using current top-down probing techniques.

After the milling, angled or vertical, the sample is oriented so that both the milled face and top surface of the sample can be viewed and/or electrically probed. The viewing and probing are used, for example, for voltage contrast imaging, electrical characterization by probing different layers and observing the electrical response using diagnostic equipment, sensing atomic force microscope probe, or observation of photonic emission.

Figure 2:
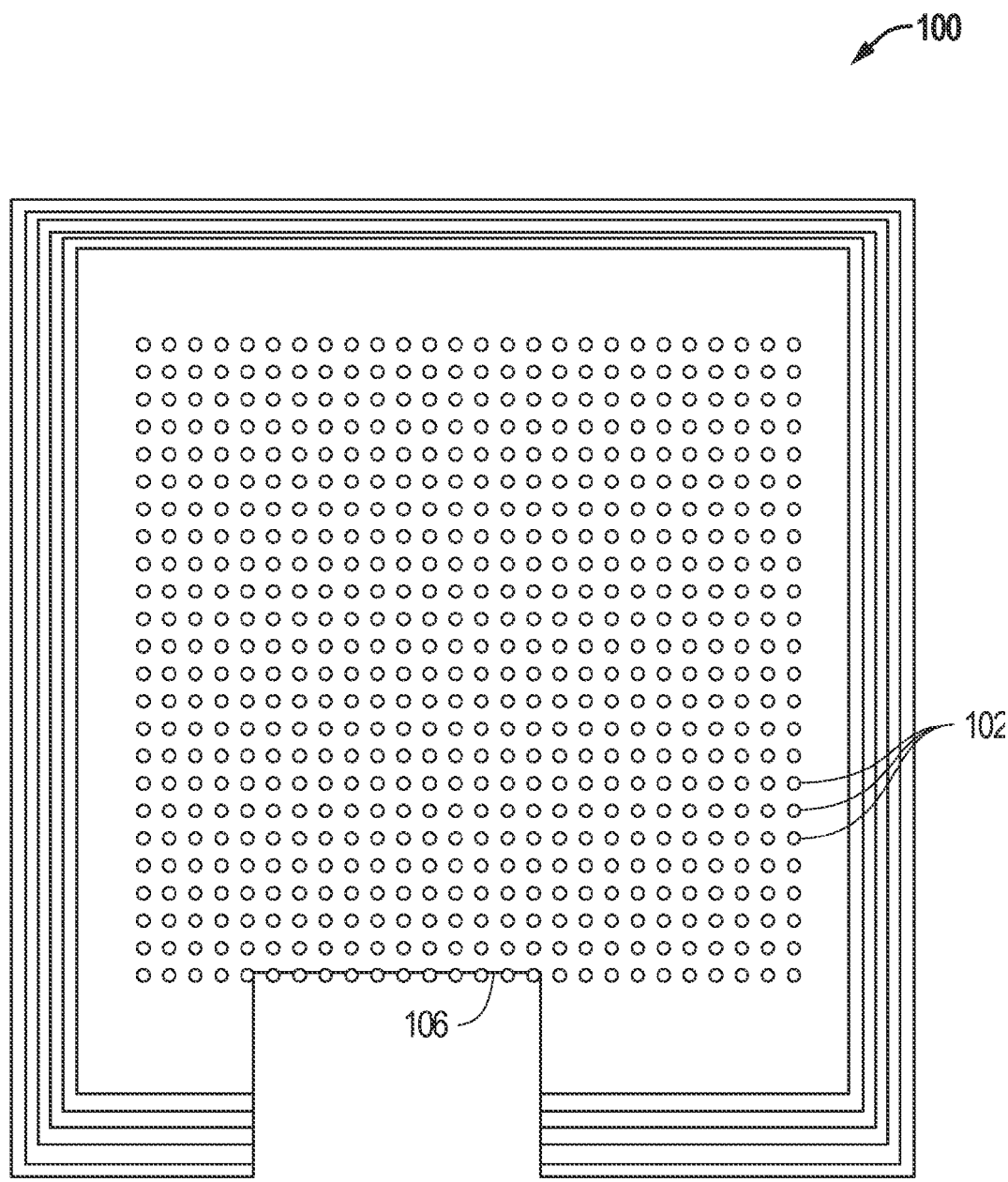
FIG. 2 is a top-down view of the 3D storage device of FIG. 1.

FIG. 1 shows a 3D storage device 100 having a trench milled therein to expose a vertical cross section. Such devices are typically encapsulated in glass (not shown). Vertical conductors 102 make electrical connections to vertically aligned elements in different horizontal layers. Patterned horizontal conductors 104 make connections in the x-y plane. Each of the three labeled conductors 104 contacts circuit elements in the same Y-Z plane (i.e., having the same x coordinate), but in different Z-planes. FIG. 1 shows a section milled out to expose a face 106. To make connections to face 106 requires a contact coming in from the side, rather than top down. It is difficult to see and manipulate a probe to provide the side access because the side of exposed vertical face is not visible from a top-down view and most probes are designed to contact a conductor from above. FIG. 2 is a top-down view of the 3D storage device. Note that while an X-Y location can be observed, no Z information is available from a top-down view of the milled face 106. In such a case, there is no reliable method of identifying if the defect is in the top layer or somewhere lower in the device stack.

Figure 3:
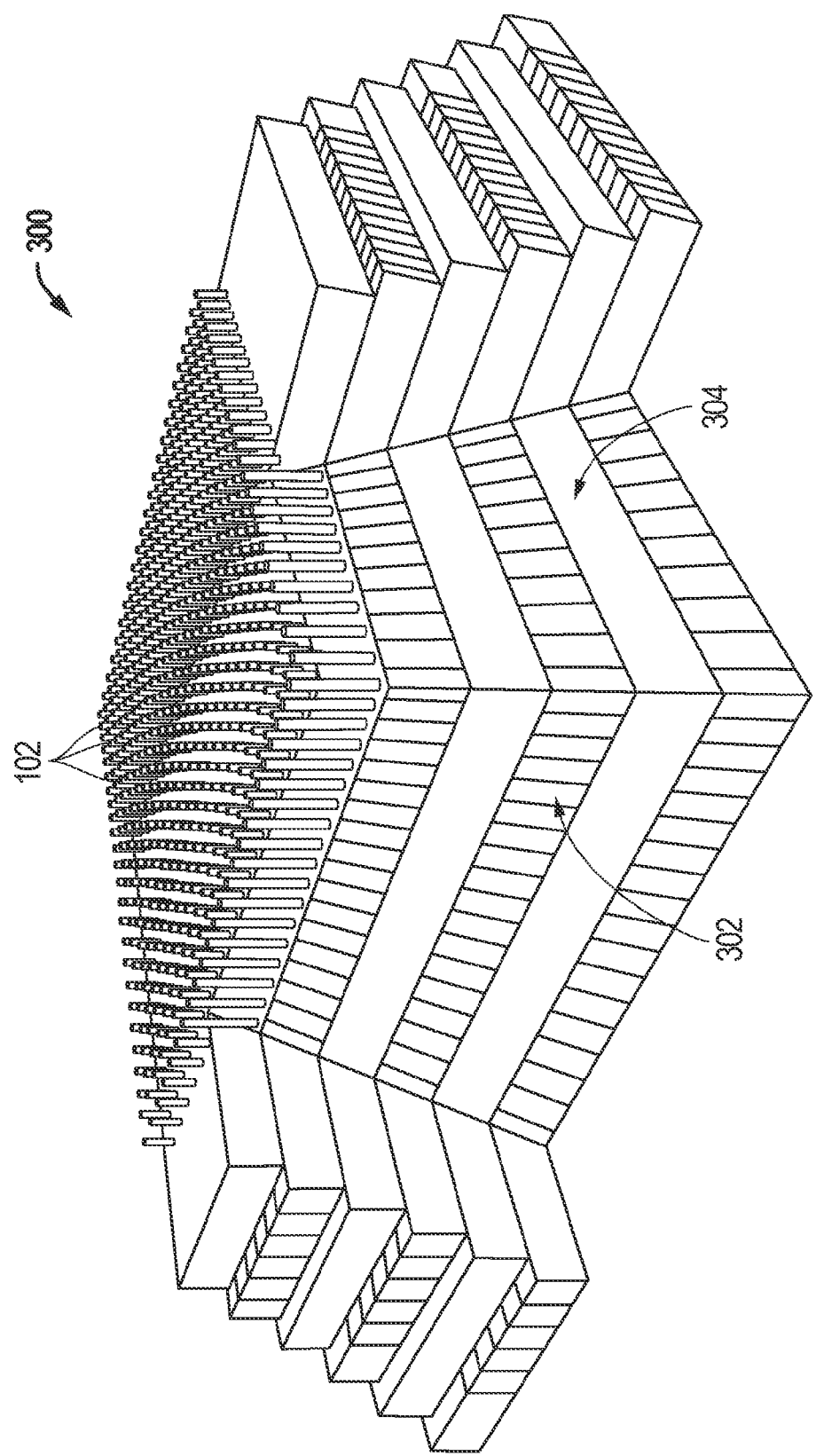
FIG. 3 shows a 3D storage device milled in accordance with an embodiment of the present invention.
Figure 4:
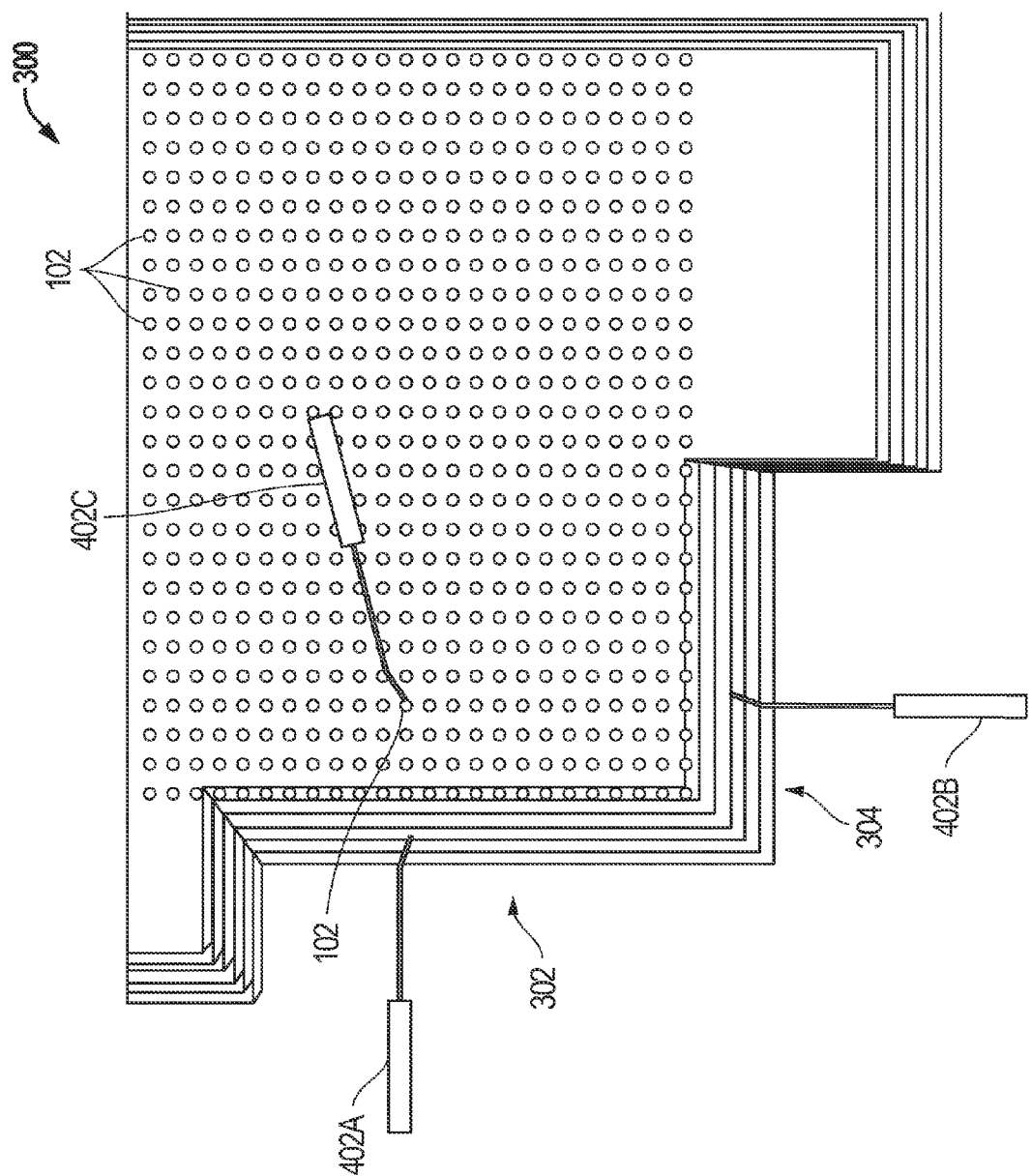
FIG. 4 is a top-down view showing the storage device of FIG. 3.

FIG. 3 shows a storage device 300 having angled mills in accordance with an embodiment of the invention that produces sloped sides 302 and 304, allowing for much easier electrical contact than the vertical face 106 of FIG. 1. FIG. 4 is a top-down view showing the angled milled surfaces 302 and 304 of device. The X-Y locations of contact points is easy to determine, as are the Z positions of the contact points in the stack. By making the various layers at different Z positions available for observation in the sloped faces, the conductor plane corresponding to the exact Z layer of interest may be identified and contacted to provide an electrical contact to the VOI. FIG. 4 shows electrical probes 402A and 402B that contact the exposed edge of internal conductors that are in electrical contact with the region of interest. Probe 402C contacts a vertical conductor 102 that is in electrical contact with the region of interest. The probes move horizontally under manual control or under control of an automated controller to a desired location, and then can move in the Z-direction, also either manually or under control of a controller, to be lowered to contact the selected conductive layer at a desired location. Electrical signals can be applied to one or more probes, while, for example, other electrical signals are sensed by one or more other probes, or a voltage contrast image is observed. The electrical probes are contacted onto the exposed conductor by lowering from above, while the process is being observed from above.

The angled mills expose contacts that allow a particular electrical component to be addressed even though that component itself is not exposed. Thus the component and neighboring components can remain intact. In some embodiments, each electrical structure represents a single bit, for example, in a 3D NAND or DRAM. The bit can be addressed using the exposed X and Y connections for the corresponding level, as well as the corresponding Z connection. The X and Y conductors for any level of Z can be easily observed from above when the conductors are exposed by the angled milling or tilted after a normal angle milling. The exposed conductors do not need to be adjacent to the structure of interest. A user can observe the number of steps in the angled mill to determine which Z level the x and y connectors are on by counting down layers.

Angled milling or tilting exposes the connection so that it can be contacted from above rather than from the side. Milling can be performed using the ion beam with or without an etch-enhancing glass, as described, for example, in U.S. patent application Ser. No. 13/921,466.

Figure 5:
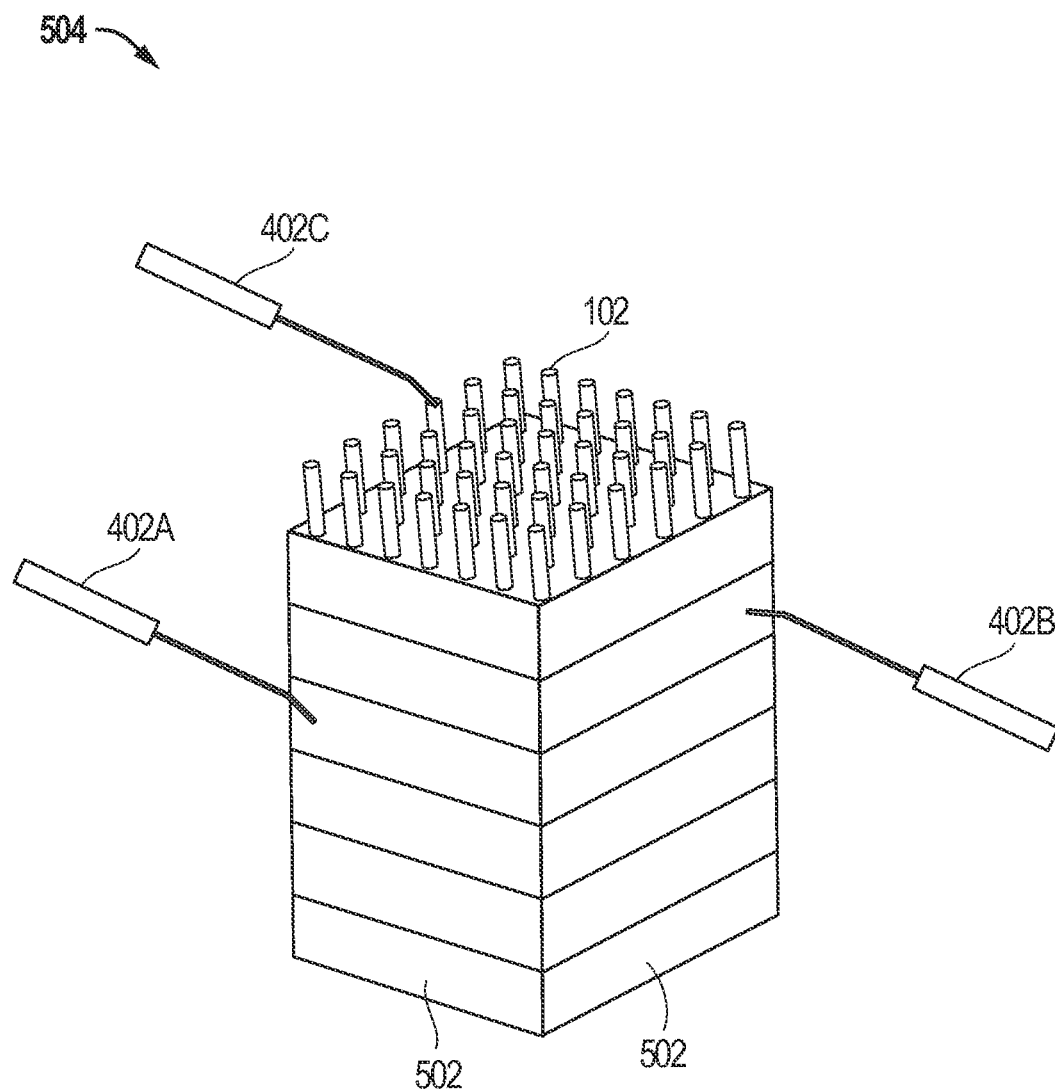
FIG. 5 shows a portion of a tilted workpiece that provides access to buried conductive layers without requiring milling at an angle to the work piece surface.

FIG. 5 shows a part of a 3D structure, analogous to the volume of FIG. 3 near the intersection of walls 302 and 304. In FIG. 5, however, the milled wall 502 and 504 are vertical. The work piece is then tilted so that a normal to each of the milled faces 502 and 504 has a component in the vertical direction. That is, the milled face 502 and 504 are visible from above and so the electrical probes 402A, 402B and 402C can be moved individually in the horizontal plane to be positioned above selected conductors and then lowered from above to contact the appropriate layer to provide an electrical connection to the region of interest. Multilayer device 504 is preferably tilted between about 30° to about 45°.

Figure 6:
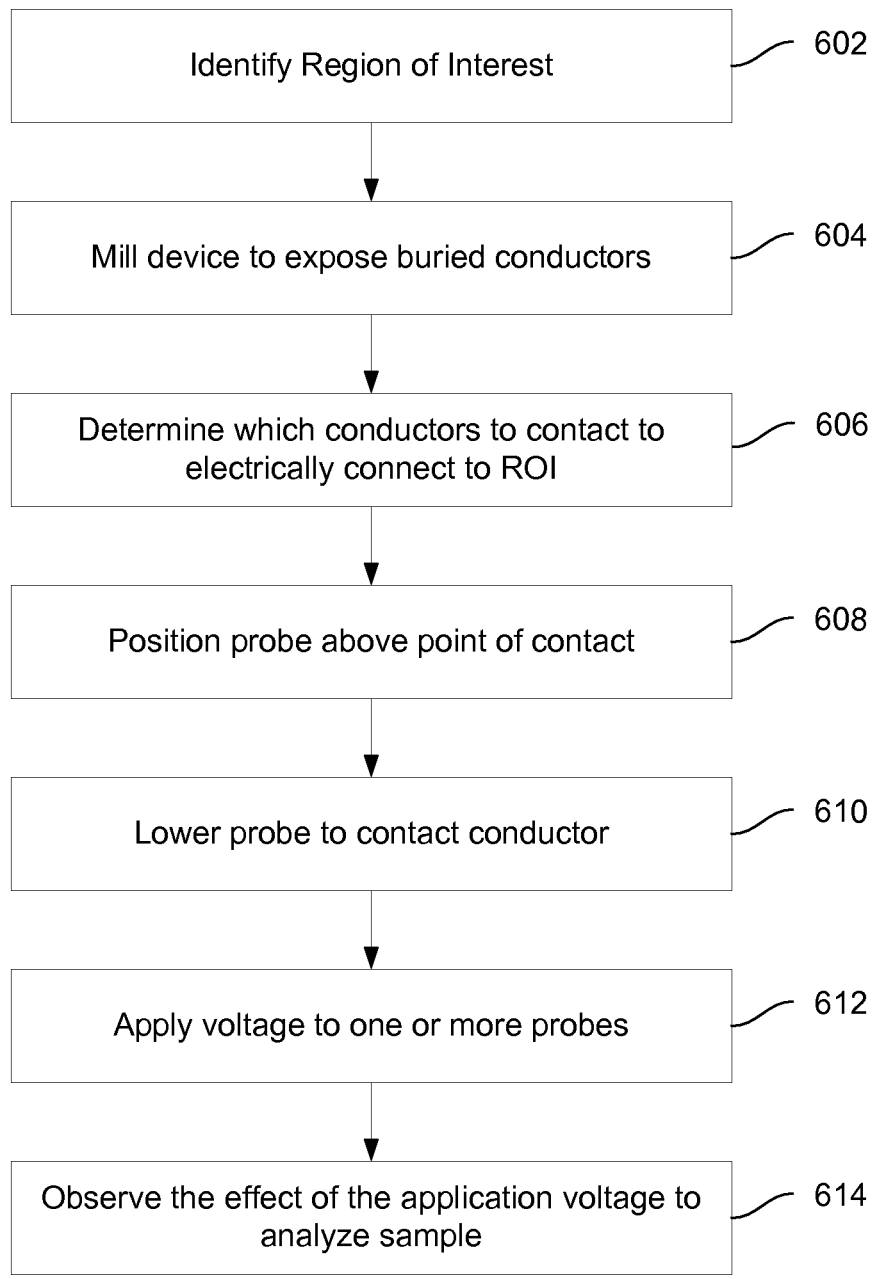
FIG. 6 is a flowchart showing the steps of an embodiment of the invention.

FIG. 6 is a flow chart showing the steps of a preferred embodiment of the invention. In step 602, a region of interest is identified. For example, the ROI may correspond to an element of a device that is found to perform poorly. The position of the ROI is determined from computer-aid-design information that maps a logic element to an electrical component and then to a physical location on the device. In step 604, the device is milled, preferably at an angle between about 30° to about 45°, to expose conductors near the region of interest. In step 606, the preferred position of probe contact is determined. For example, the layout of the chip is checked to determine which conductor on which conductive layer makes contact with the region of interest. The identified conductive layer can be identified by counting down from the top of the chip to the appropriate level, since the angled mill provides visibility of the multiple levels. In step 608, electrical probes are moved in the X-Y direction to position the probes appropriately as determined in step 606, and then in step 610, the probes are lowered in the Z direction to contact electrical conductors at or near the region of interest. It is understood that the probe motion may not be simple rectangular X-Y-Z motion, but the probe will move through space and downward to contact the electrical conductor. As used here, moving in the X-Y direction or Z direction does not require separate motions in the mentioned planes or direction, but includes rotations and simultaneous motions in different directions that accomplish the same result. In step 612, voltages or currents are applied to the sample through one or more of the probes. In step 614, the effect of the applied voltage or current is observed. Observing the effect can include, for example, sensing voltages or currents from one or more of the probes, observing the region of interest using voltage contrast imaging, micro-Raman analysis, or other imaging or analytical technique.

Additional processing can be applied to the exposed layers, for example, using circuit edit-type techniques, such as passivating, depositing an insulator on part of the sample, cutting circuits, and depositing conductors to change behavior or creating probing points. Circuit edit-type techniques are well known. For example, a conductor can be deposited by beam-induced deposition to connect two or more exposed layers. An insulator can be deposited by beam-induced deposition before the conductor deposition to electrically other exposed layers of the integrated circuit from the deposited conductor. Exposed conductors can also be cut to with the ion beam to break an electrical contact.

Figure 7:
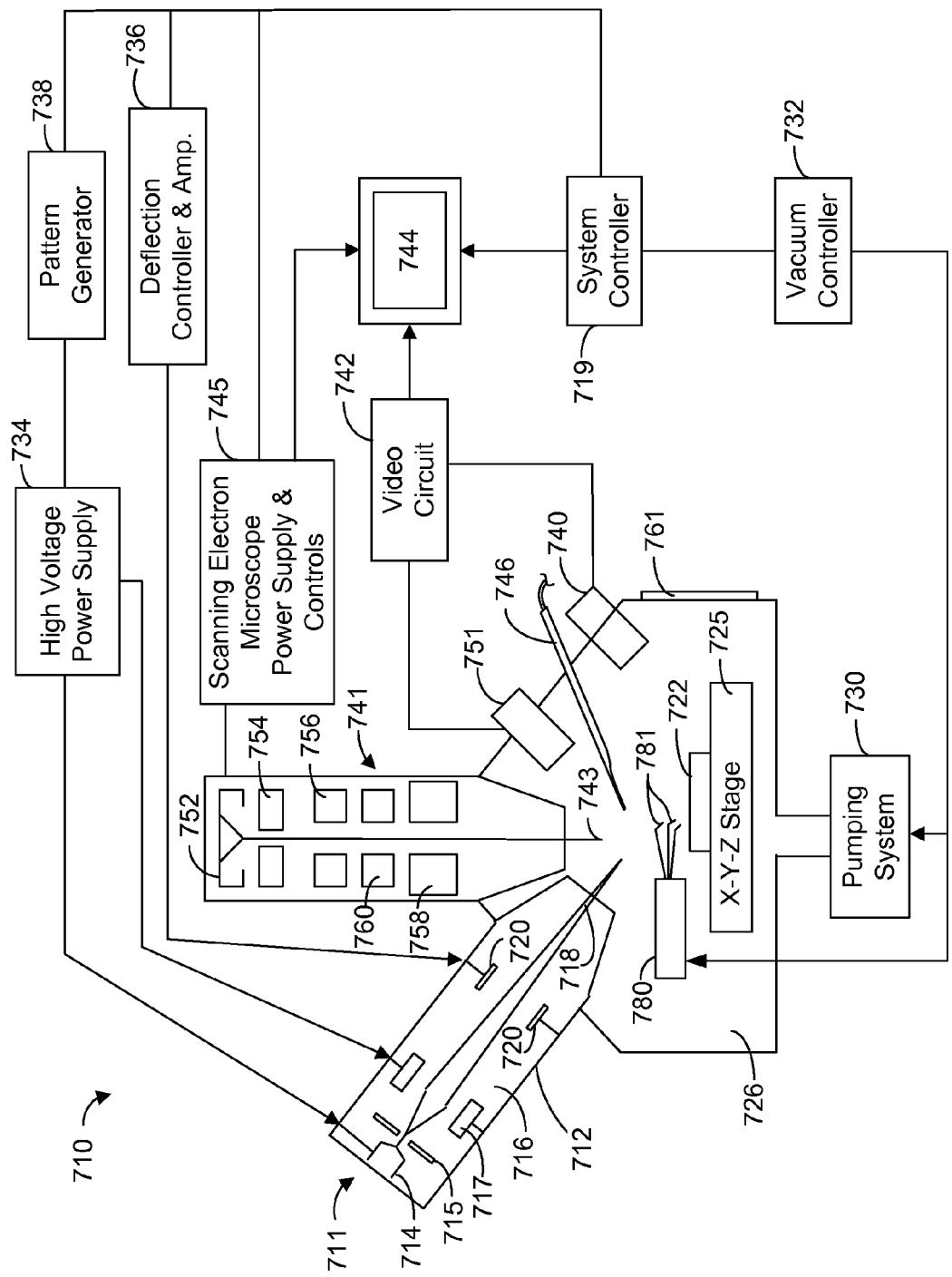
FIG. 7 shows schematically a dual beam system that can be used to implement the present invention.

FIG. 7 shows a typical dual beam system 710 suitable for practicing the present invention, with a vertically mounted SEM column and a FIB column mounted at an angle of approximately 52° from the vertical. Suitable dual beam systems are commercially available, for example, from FEI Company, Hillsboro, Oreg., the assignee of the present application. While an example of suitable hardware is provided below, the invention is not limited to being implemented in any particular type of hardware.

A scanning electron microscope 741, along with power supply and control unit 745, is provided with the dual beam system 710. An electron beam 743 is emitted from a cathode 752 by applying voltage between cathode 752 and an anode 754. Electron beam 743 is focused to a fine spot by means of a condensing lens 756 and an objective lens 758. Electron beam 743 is scanned two-dimensionally on the specimen by means of a deflection coil 760. Operation of condensing lens 756, objective lens 758, and deflection coil 760 is controlled by power supply and control unit 745.

Electron beam 743 can be focused onto substrate 722, which is on movable stage 725 within lower chamber 726. When the electrons in the electron beam strike substrate 722, secondary electrons are emitted. These secondary electrons are detected by a secondary electron detector 740 as discussed below.

Dual beam system 710 also includes focused ion beam (FIB) system 711 which comprises an evacuated chamber having an upper portion 712 within which are located an ion source 714 and a focusing column 716 including extractor electrodes and an electrostatic optical system. The axis of focusing column 716 is tilted 52 degrees from the axis of the electron column. The upper portion 712 includes an ion source 714, an extraction electrode 715, a focusing element 717, deflection elements 720, and a focused ion beam 718. Ion beam 718 passes from ion source 714 through focusing column 716 and between electrostatic deflectors 720 toward substrate 722, which comprises, for example, a semiconductor device positioned on movable stage 725 within lower chamber 726.

Stage 725 can preferably move in a horizontal plane (X and Y axes) and vertically (Z axis). Stage 725 can also tilt approximately 60° and rotate about the Z axis. A door 761 is opened for inserting substrate 722 onto X-Y stage 725 and also for servicing an internal gas supply reservoir, if one is used. The door is interlocked so that it cannot be opened if the system is under vacuum.

An ion pump (not shown) is employed for evacuating upper portion 712. The chamber 726 is evacuated with turbomolecular and mechanical pumping system 730 under the control of vacuum controller 732. The vacuum system provides within chamber 726 a vacuum of between approximately $1\times10^{-7}$ Torr and $5\times10^{-4}$ Torr. If an etch-assisting gas, an etch-retarding gas, or a deposition precursor gas is used, the chamber background pressure may rise, typically to about $1\times10^{-5}$ Torr.

The high voltage power supply provides an appropriate acceleration voltage to electrodes in ion beam focusing column focusing 716 for energizing and focusing ion beam 718. When it strikes substrate 722, material is sputtered, that is physically ejected, from the sample. Alternatively, ion beam 718 can decompose a precursor gas to deposit a material.

High voltage power supply 734 is connected to liquid metal ion source 714 as well as to appropriate electrodes in ion beam focusing column 716 for forming an approximately 1 keV to 60 keV ion beam 718 and directing the same toward a sample. Deflection controller and amplifier 736, operated in accordance with a prescribed pattern provided by pattern generator 738, is coupled to deflection plates 720 whereby ion beam 718 may be controlled manually or automatically to trace out a corresponding pattern on the upper surface of substrate 722. In some systems the deflection plates are placed before the final lens, as is well known in the art. Beam blanking electrodes (not shown) within ion beam focusing column 716 cause ion beam 718 to impact onto blanking aperture (not shown) instead of substrate 722 when a blanking controller (not shown) applies a blanking voltage to the blanking electrode.

The liquid metal ion source 714 typically provides a metal ion beam of gallium. The source typically is capable of being focused into a sub one-tenth micrometer wide beam at substrate 722 for either modifying the substrate 722 by ion milling, enhanced etch, material deposition, or for the purpose of imaging the substrate 722. Other ion sources, such as a plasma ion source, can also be used.

A probe assembly includes a probe motion mechanism 780 and probe tips 781. The probe tips can be moved individually to a desired position and lowered to contact the substrate 722. While three probe tips are shown, the number of probe tips can vary. Multiple probe motion mechanism can be used to control any number of probes. The probe tips can apply a voltage or current to the substrate 722 at a precise location and/or can sense a voltage or current. In some embodiments, the probes are mounted on a ring around the work piece.

A charged particle detector 740, such as an Everhart-Thornley detector or multi-channel plate, used for detecting secondary ion or electron emission is connected to a video circuit 742 that supplies drive signals to video monitor 744 and receives deflection signals from controller 719. The location of charged particle detector 740 within lower chamber 726 can vary in different embodiments. For example, a charged particle detector 740 can be coaxial with the ion beam and include a hole for allowing the ion beam to pass. In other embodiments, secondary particles can be collected through a final lens and then diverted off axis for collection.

An optical microscope 751 allows observation of the sample 722 and the probes 781. The optical microscope may be co-axial with one of the charged particle beams, as described, for example, in U.S. Pat. No. 6,373,070 to Rasmussen, for "Method apparatus for a coaxial optical microscope with focused ion beam," is assigned to the applicant of the present application.

A gas delivery system 746 extends into lower chamber 726 for introducing and directing a gaseous vapor toward substrate 722. U.S. Pat. No. 5,851,413, to Casella et al. for "Gas Delivery Systems for Particle Beam Processing," assigned to the assignee of the present invention, describes a suitable gas delivery system 746. Another gas delivery system is described in U.S. Pat. No. 5,435,850, to Rasmussen for a "Gas Injection System," also assigned to the assignee of the present invention. For example, a metal organic compound can be delivered to the beam impact point to deposit a metal upon impact of the ion beam or the electron beam. A precursor gas, such as $(CH_3)_3Pt(C_pCH_3)$ to deposit platinum or tungsten hexcarbonyl to deposit tungsten, can be delivered to be decomposed by the electron beam to provide the protective layer in step 108.

A system controller 719 controls the operations of the various parts of dual beam system 710. Through system controller 719, a user can cause ion beam 718 or electron beam 743 to be scanned in a desired manner through commands entered into a conventional user interface (not shown). Alternatively, system controller 719 may control dual beam system 710 in accordance with programmed instructions. A preferred controller is in communication with or includes a memory that stores instructions for automatically carrying out the steps of FIG. 6. System controller 719 can be used to control the probe motion assembly 780. In some embodiments, dual beam system 710 incorporates image recognition software, such as software commercially available from Cognex Corporation, Natick, Mass., to automatically identify regions of interest, and then the system can manually or automatically expose cross sections for imaging in accordance with the invention. For example, the system could automatically locate similar features on semiconductor wafers including multiple devices, and expose and form images of features of interest on different (or the same) devices.

The invention has broad applicability and can provide many benefits as described and shown in the examples above. The embodiments will vary greatly depending upon the specific application, and not every embodiment will provide all of the benefits and meet all of the objectives that are achievable by the invention. Particle beam systems suitable for carrying out the present invention are commercially available, for example, from FEI Company, the assignee of the present application.

Descriptions herein use the terms horizontal and vertical relative to a wafer or other work piece. It will be understood that "horizontal" typically is used to mean parallel to the work piece surface and the conductive planes deposited on to the work piece, and "vertical" is typically used to mean orthogonal to the work piece surface.

The invention has broad applicability and can provide many benefits as described and shown in the examples above. The embodiments will vary greatly depending upon the specific application, and not every embodiment will provide all of the benefits and meet all of the objectives that are achievable by the invention. Particle beam systems suitable for carrying out the present invention are commercially available, for example, from FEI Company, the assignee of the present application.

The present specification discloses both a method and an apparatus for performing the operations of the method. Such apparatus may be specially constructed for the required purposes, or may comprise a general purpose computer or other device selectively activated or reconfigured by a computer program stored in the computer. Various general purpose charged particle beam systems may be used with programs in accordance with the teachings herein. Alternatively, the construction of more specialized apparatus to perform the required method steps may be appropriate.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Such a computer program may be stored on any computer readable medium. The computer readable medium may include storage devices such as magnetic or optical disks, memory chips, or other storage devices suitable for interfacing with a general purpose computer. The computer readable medium may also include a hard-wired medium such as exemplified in the Internet system, or wireless medium such as exemplified in the GSM mobile telephone system. The computer program when loaded and executed on such a general-purpose computer or controller for a charged particle beam and effectively results in an apparatus that implements the steps of the preferred method.

The invention may also be implemented as hardware modules. More particular, in the hardware sense, a module is a functional hardware unit designed for use with other components or modules. For example, a module may be implemented using discrete electronic components, or it can form a portion of an entire electronic circuit such as an Application Specific Integrated Circuit (ASIC). Numerous other possibilities exist. Those skilled in the art will appreciate that the system can also be implemented as a combination of hardware and software modules.

Although much of the previous description is directed at semiconductor wafers, the invention could be applied to any suitable substrate or surface. Further, whenever the terms "automatic," "automated," or similar terms are used herein, those terms will be understood to include manual initiation of the automatic or automated process or step. In the following discussion and in the claims, the terms "including" and "comprising" are used in an open-ended fashion, and thus should be interpreted to mean "including, but not limited to . . . ."

To the extent that any term is not specially defined in this specification, the intent is that the term is to be given its plain and ordinary meaning. The accompanying drawings are intended to aid in understanding the present invention and, unless otherwise indicated, are not drawn to scale.

The term "integrated circuit" refers to a set of electronic components and their interconnections (internal electrical circuit elements, collectively) that are patterned on the surface of a microchip. The term "semiconductor chip" refers generically to an integrated circuit (IC), which may be integral to a semiconductor wafer, separated from a wafer, or packaged for use on a circuit board. The term "FIB" or "focused ion beam" is used herein to refer to any collimated ion beam, including a beam focused by ion optics and shaped ion beams.

The embodiment above describes 3D NAND type structures, but the invention is not limited to such structures and is useful, for example, for DRAMS, and for characterizing trenches and other structures, as well as circular holes.

To the extent that any term is not specially defined in this specification, the intent is that the term is to be given its plain and ordinary meaning. The accompanying drawings are intended to aid in understanding the present invention and, unless otherwise indicated, are not drawn to scale.

Some embodiments of the invention provide a method of analyzing a region of interest in a three dimensional integrated circuit structure having multiple layers of conductive materials, comprising directing a focused ion beam toward the three dimensional integrated circuit structure at a non-normal angle to the layers of conductive material to expose multiple horizontal conductive layers; determining which exposed horizontal conductor corresponds to the vertical position of a component of interest; moving one or more electrical probes to contact the exposed horizontal conductor from above; applying a voltage to the electrical probe; and observing the effect of the applied voltage to analyze the region of interest.

In some embodiments, directing a focused ion beam toward the three dimensional integrated circuit structure includes directing the focused ion beam to leave the region of interest intact while expose multiple horizontal conductive layers to provide electrical access to the region of interest.

In some embodiments, moving one or more electrical probes to contact the exposed horizontal conductor includes moving one or more of the electrical probes to position the probed over the exposed horizontal conductor and then moving the probe in a direction having a vertical component to contact the exposed horizontal conductor.

In some embodiments, the three dimensional structure comprises a data storage circuit.

In some embodiments, the three dimensional structure comprises a Logic circuit and/or a NAND, a SRAM, a DRAM, or a memory cell.

Some embodiment provide a method of analyzing a region of interest in a three dimensional integrated circuit structure, comprising directing a focused ion beam toward the three dimensional integrated circuit structure to mill a surface exposing multiple horizontal conductive layers; determining which exposed horizontal conductive layer corresponds to the vertical position of a region of interest; lowering an electrical probe to contact a conductor that is in the determined horizontal conductive layer and that corresponds to a region of interest; applying a voltage to the electrical probe; and observing the effect of the applied voltage to analyze the region of interest.

In some embodiments, directing a focused ion beam toward the three dimensional integrated circuit structure to mill a surface exposing multiple horizontal conductive layers includes directing the focused ion beam normal to the work piece surface and the embodiment further comprises tilting the work piece so that a normal to the milled surface has a vertical component.

In some embodiments, tilting the work piece includes tilting the work piece at an angle of between about 30° to about 45°.

In some embodiments, directing a focused ion beam toward the three dimensional integrated circuit structure to mill a surface exposing multiple horizontal conductive layers includes directing the focused ion beam at a non-normal angle to the horizontal conductive layers.

In some embodiments, directing the focused ion beam at a non-normal angle to the horizontal conductive layers includes directing the focused ion beam at an angle of between about 30° to about 45° to the horizontal conductive layers.

In some embodiments, observing the effect of the applied voltage to analyze the region of interest includes using voltage contrast imaging, sensing an electrical signal, or using an atomic force microscope probe.

In some embodiments, sensing an electrical signal comprises sensing a voltage or current using an electrical probe or probes.

Some embodiments provide a system for analyzing a region of interest in a three-dimensional integrated circuit, comprising an ion optical column for providing a focused beam of ions; an electron optical column for providing a focused beam of electrons; a particle detector for detecting secondary particles emitted from the sample; an electrical probe movable in three dimensions for contacting the integrated circuit and providing electrical contact to the region of interest; a controller communicating to a computer memory, the computer memory storing instructions for directing a focused ion beam toward the three dimensional integrated circuit structure to mill a surface exposing multiple horizontal conductive layers; determining which exposed horizontal conductive layer corresponds to the vertical position of a region of interest; lowering an electrical probe to contact a conductor that is in the determined horizontal conductive layer and that corresponds to a region of interest; applying a voltage to the electrical probe; and observing the effect of the applied voltage to analyze the region of interest.

In some embodiments, the computer instructors for directing the focused ion beam toward the three dimensional integrated circuit structure includes computer instruction for directing the focused ion beam at a non-normal angle to the horizontal conductive layers.

In some embodiments, the computer instructors for directing the focused ion beam toward the three dimensional integrated circuit structure includes directing the focused ion beam normal to the work piece surface and further comprise computer instructions for tilting the work piece so that a normal to the milled surface has a vertical component.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of analyzing a region of interest in a three-dimensional integrated circuit structure having multiple conductive layers extending in a horizontal direction for providing electrical access through at least one conductive layer to the region of interest, comprising:
    directing a focused ion beam toward the three-dimensional integrated circuit structure to produce a milled surface away from the region of interest and comprising a plurality of exposed conductive layers extending in a horizontal direction;
    moving at least one electrical probe to contact from above the milled surface of at least one selected exposed conductive layer extending in a horizontal direction;
    applying a voltage to said at least one electrical probe; and
    observing an effect of the applied voltage to analyze the region of interest; wherein:
    performing said directing of a focused ion beam in one of the following ways:
        at a non-normal angle to said horizontal direction; or
        at a normal angle to said horizontal direction, after which the circuit structure is tilted so that a normal to the milled surface has a vertical component; and
    determining, in said plurality of exposed conductive layers, by vertical position the at least one selected exposed conductive layer extending in a horizontal direction that provides electrical access to the region of interest away from the milled surface.

2. The method of claim 1 in which directing a focused ion beam toward the circuit structure includes directing the focused ion beam to leave the region of interest intact and undamaged while producing the milled surface.

3. The method of claim 1 in which moving at least one electrical probe to contact from above the milled surface of at least one selected exposed conductive layer includes moving the at least one electrical probe to position the probe over the milled surface of the least one selected exposed conductive layer and then moving the probe in a direction having a vertical component to contact the milled surface of the at least one selected exposed conductive layer.

4. The method of claim 1 in which directing a focused ion beam at a non-normal angle to said horizontal direction includes directing the focused ion beam at an angle of between about 30° to about 45° from a normal to said horizontal direction.

5. The method of claim 1 in which observing an effect of the applied voltage to analyze the region of interest comprises observing the effect in using voltage contrast imaging, observing the effect through sensing an electrical signal, or observing the effect in using an atomic force microscope probe.

6. The method of claim 5 in which, when observing the effect is through sensing an electrical signal, the sensing the electrical signal comprises sensing a voltage or current using an electrical probe or probes.

7. The method of claim 1 in which the three dimensional structure comprises a data storage circuit.

8. The method of claim 1 in which the three dimensional structure comprises a Logic circuit or comprises a Logic circuit and at least one of a NAND, a SRAM, a DRAM, or a memory cell.

9. A method of analyzing a region of interest in a three dimensional integrated circuit structure having conductive layers extending in a horizontal direction for providing electrical access through at least one conductive layer to the region of interest, comprising:
    directing a focused ion beam toward the circuit structure to mill a surface away from the region of interest and comprising a plurality of exposed conductive layers extending in a horizontal direction;
    determining by vertical position which exposed conductive layer extending in a horizontal direction provides electrical access to the region of interest away from the milled surface;
    lowering an electrical probe to contact the milled surface of the exposed conductive layer extending in a horizontal direction that provides electrical access to the region of interest;
    applying a voltage to the electrical probe; and
    observing an effect of the applied voltage to analyze the region of interest.

10. The method of claim 9 in which directing a focused ion beam toward the circuit structure to mill a surface away from the region of interest and comprising a plurality of exposed conductive layers extending in a horizontal direction includes directing the focused ion beam at a normal angle to said horizontal direction and further comprising tilting the work piece so that an angle normal to the milled surface has a vertical component.

11. The method of claim 10 in which tilting the work piece includes tilting the work piece at an angle of between about 30° to about 45°.

12. The method of claim 9 in which directing a focused ion beam toward the circuit structure to mill a surface away from the region of interest and comprising a plurality of exposed conductive layers extending in a horizontal direction includes directing the focused ion beam at a non-normal angle to said horizontal direction.

13. The method of claim 12 in which directing the focused ion beam at a non-normal angle to said horizontal direction includes directing the focused ion beam at an angle of between about 30° to about 45° to said horizontal direction.

14. The method of claim 9 in which observing an effect of the applied voltage to analyze the region of interest comprises observing the effect in using voltage contrast imaging, observing the effect through sensing an electrical signal, or observing the effect in using an atomic force microscope probe.

15. The method of claim 14 in which, when observing the effect is through sensing an electrical signal, the sensing the electrical signal comprises sensing a voltage or current using an electrical probe or probes.

16. A system for analyzing a region of interest in a three-dimensional integrated circuit structure having conductive layers extending in a horizontal direction, comprising:
- an ion optical column for providing a focused ion beam;
- an electron optical column for providing a focused electron beam;
- a particle detector for detecting secondary particles emitted from the structure;
- an electrical probe movable in three dimensions for contacting the integrated circuit structure and providing electrical contact to the region of interest;
- a controller communicating to a computer memory, the computer memory storing instructions for operations comprising:
  - directing a focused ion beam toward the circuit structure to mill a surface away from the region of interest and comprising a plurality of exposed conductive layers extending in a horizontal direction;
  - determining by vertical position which exposed conductive layer extending in a horizontal direction provides electrical access to the region of interest away from the milled surface;
  - lowering an electrical probe to contact the milled surface of the exposed conductive layer extending in a horizontal direction that provides electrical access to the region of interest;
  - applying a voltage to the electrical probe; and
  - observing an effect of the applied voltage to analyze the region of interest.

17. The system of claim 16 in which the computer instructions for directing the focused ion beam toward the circuit structure include instruction for directing the focused ion beam at a non-normal angle to said horizontal direction.

18. The system of claim 16 in which the computer instructions for directing the focused ion beam toward the circuit structure include instruction for directing the focused ion beam at an angle normal to said horizontal direction and, for the computer memory storing instructions for operations, the operations further comprising tilting the work piece so that an angle normal to the milled surface has a vertical component.

19. The method of claim 1, wherein:
- directing a focused ion beam toward the-three-dimensional integrated circuit structure comprises directing a focused ion beam toward a three-dimensional integrated circuit having transistors on multiple levels and having an array of vertical conductors contacting the transistor on the multiple levels; and
- further comprising applying a voltage to one or more of the vertical conductors in electrical connection with the region of interest or in which observing an effect of the applied voltage comprises observing a voltage on the one or more vertical conductors.

20. The method of claim 9, wherein:
- directing a focused ion beam toward the-three-dimensional integrated circuit structure comprises directing a focused ion beam toward a three-dimensional integrated circuit having transistors on multiple levels and having an array of vertical conductors contacting the transistor on the multiple levels; and
- further comprising applying a voltage to one or more of the vertical conductors in electrical connection with the region of interest or in which observing an effect of the applied voltage comprises observing a voltage on the one or more vertical conductors.

21. The system of claim 16 in which the system further comprises an additional electrical probe for contacting a vertical conductor that makes electrical connections to vertically aligned elements in different conductive layers extending in a horizontal direction, and wherein the vertical conductor is in electrical connection with the region of interest.

* * * * *